United States Patent [19]
Isowa et al.

[11] Patent Number: 5,180,712

[45] Date of Patent: * Jan. 19, 1993

[54] PETIDE ANTIDEMENTIA AND NOOTROPIC AGENTS

[75] Inventors: Yoshikazu Isowa; Yoshiaki Sato; Yoshiharu Nakashima, all of Tokyo; Mitsuo Masaki, Chiba; Norihisa Miyake, Saitama; Masaki Uehara, Saitama; Kenji Hirate, Saitama, all of Japan

[73] Assignees: Fujirebio Kabushiki Kaisha; Nippon Chemiphar Co., Ltd., both of Tokyo, Japan

[*] Notice: The portion of the term of this patent subsequent to May 12, 2009 has been disclaimed.

[21] Appl. No.: 393,572

[22] Filed: Aug. 14, 1989

[30] Foreign Application Priority Data

Aug. 12, 1988 [JP] Japan .................................. 63-201358
Aug. 12, 1988 [JP] Japan .................................. 63-201359

[51] Int. Cl.$^5$ .................... A61K 37/02; C07K 5/10; C07K 7/06
[52] U.S. Cl. ........................ 514/16; 514/17; 514/18; 530/315; 530/329; 530/330
[58] Field of Search ................ 424/565; 514/16, 17, 514/18; 530/300, 315, 330, 329

[56] References Cited

U.S. PATENT DOCUMENTS 4,487,765 12/1984 de Wied ............................. 424/177

FOREIGN PATENT DOCUMENTS 0161017 11/1985 Netherlands .

OTHER PUBLICATIONS

Burbach et al., A Major Metabolite of Arginme Vasopressin in the Brain is a Highly Potent Neuropeptide, *Science* 221: 1310–1312, (1983).

Stedman, Stedman's Medical Dictionary, 24th Ed. (1982).

Psychopharmacology (1982) 78:104–111, "Effects of the Novel Compound Aniracetam (Ro 13-5057) Upon Impaired Learning and Memory in Rodents".

Recl. Trav. Chim. Pays-Bas 103, 68–74 (1984), "Synthesis of Fragments of Arginine Vasopressin and Oxytocin Containing a Cystine Residue . . . ".

Collection Czechoslovak Chem. Commun. (vol. 53) (188), "Formation of Open-Chain Asymmetrical Cystine Peptides on a Solid Support . . . ".

*Primary Examiner*—Robert A. Wax
*Assistant Examiner*—Stephen Walsh
*Attorney, Agent, or Firm*—McAulay Fisher Nissen Goldberg & Kiel

[57] ABSTRACT

A peptide having one of the following formulae (I), (II), (III) and (IV):

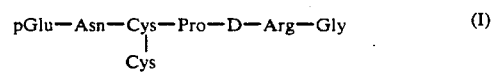

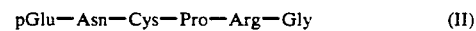

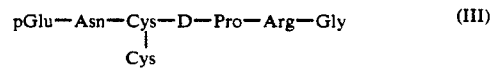

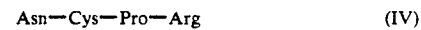

or its functional derivatives, and a pharmaceutically acceptable salt thereof are disclosed. These peptides have a nootropic effect and are effective as antidementia agents.

16 Claims, No Drawings

PETIDE ANTIDEMENTIA AND NOOTROPIC AGENTS

BACKGROUND OF THE INVENTION

1. Field of the Invention

The present invention relates to novel peptides having a nootropic effect and an anti-dementia agent containing the same.

2. Description of Prior Art

Vasopressin has been previously known as a compound having a nootropic effect, i.e., intelligence developing effect. Recently, it has been reported that a peptide seemingly corresponding to a vasopressin fragment, for example, one having the following formula:

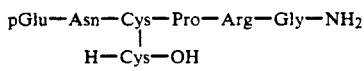

has a nootropic effect similar to that of vasopressin as reported in Science, 221, pp.1310–1312 (1983).

Further, Japanese Patent Provisional Publication No. 59(1984)-93036 describes that a peptide having the formula:

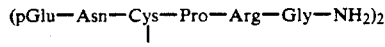

also has a nootropic effect.

SUMMARY OF INVENTION

It is an object of the present invention to provide new peptides having a nootropic effect which are superior to the known vasopressin as well as to the known peptides corresponding to vasopressin fragments.

The present invention provides a peptide having one of the following formulae (I), (II), (III) and (IV):

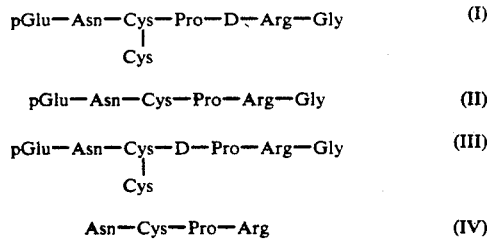

and its functional derivatives. The novel peptides of the invention can be in the form of their pharmaceutically acceptable salts.

The above-mentioned peptides, their functional derivatives, and their pharmaceutically acceptable salts show a prominent nootropic effect in passive avoidance tests using rats, and are expected to be prominently effective as active component of pharmaceutical agent for prevention or treatment of senile dementia (Alzheimer's dementia), cerebrovascular dementia and other dementia diseases.

DETAILED DESCRIPTION OF THE INVENTION

The peptides of the invention have one of the aforementioned formulae (I), (II), (III) and (IV) and may be in the form of their functional derivatives.

Examples of the functional derivatives of the peptides of the formulae (I), (II), (III) and (IV) include the following derivatives:

a) N-acyl derivatives having N-acyl group(s) as the functional group(s); N-acyl group is derived from an aliphatic carboxylic acid having 1 to 6 carbon atoms, preferably one derived from acetic acid; the N-acyl group can be expressed by —NHCOR (wherein R is an alkyl group having 1–5 carbon atoms), b) derivatives having, as the functional group(s), groups in the form of amides, or monoalkyl or dialkyl substituted-amides having alkyl chain(s) of 1 to 6 carbon atoms; which can be expressed by —CONH$_2$, —CONHR, and —CONR$_2$ (wherein R is an alkyl group having 1–6 carbon atoms), and c) derivatives having, as the functional group(s), groups in the form of esters derived from alcohol having 1 to 18 carbon atoms, preferably those derived from an aliphatic alcohol having 1 to 6 carbon atoms; which can be expressed by —COOR (wherein R is an alkyl group having carbon 1–18 atoms, preferably 1–6 carbon atoms).

As the examples of pharmaceutically acceptable salts of the peptides or their derivatives, acid addition salts and basic salts such as alkali metal salts and ammonium salts can be mentioned. Examples of such acid addition salts include salts of inorganic acids (e.g., hydrochloric acid, sulfuric acid and phosphoric acid) or of organic acids (e.g., acetic acid, propionic acid, citric acid, tartaric acid, malic acid, oxalic acid and methanesulfonic acid). Examples of basic salts include sodium salt, potassium salt, and triethylamine salt.

In the specification, the peptides are described by abbreviations commonly used in the field of chemistry, or abbreviations recommended by the IUPAC-IUB Commission on Biochemical Nomenclature. For example, the following symbols are used in the specification. The amino acids should be construed to be of the L-type, unless specific description with respect to optical configuration is given.

Asn: asparagine
Arg: arginine
Cys: cysteine
Gly: glycine
pGlu: pyroglutamic acid
Pro: proline
Boc: t-butoxycarbonyl
Z: benzyloxycarbonyl
Mbs: p-methoxybenzenesulfonyl
MBzl: p-methoxybenzyl
Acm: Acetamidomethyl
Scm: S-carbomethoxysulfenyl
OBzl: benzyl ester
OSu: N-hydroxysuccinimide ester The compounds of the present invention can be prepared by the methods conventionally employed in peptide chemistry. For example, they can be prepared by those processes described in Schröder and Lübke, *The Peptides*, Vol 1, Academic Press, New York, 1965, and Nobuo Izumiya et al., *Fundamental and Experiment of Peptide Synthesis*, Maruzen, Tokyo, 1985, and can be prepared by either the solution synthesis or the solid phase synthesis.

Examples of the methods for formation of the peptide bonds include azide method, acid chloride method, symmetrical anhydride method, mixed anhydride method, N,N'-dicyclohexylcarbodiimide method, N,N'-dicyclohexylcarbodiimido-additive method, activated ester method, carbonyldiimidazole method, oxidation-reduction method, and the method employing a Woodward reagent K.

In the synthesis of a peptide, the cystine moiety which is an amino acid forming the peptide of the invention can be formed by employing a cystine derivative or by converting a cysteine moiety of the peptide chain into a cystine moiety after the formation of the peptide chain by the conventional method.

Before carrying out the coupling reaction, carboxyl group, amino group, guanidino group and mercapto group and the like which do not participate in the reaction can be protected, and those which participate in the coupling reaction can be activated, both by the methods well known in the art.

Examples of the protecting groups for the carboxyl group include ester-forming groups such as methyl, ethyl, benzyl, p-nitrobenzyl, t-butyl and cyclohexyl.

Examples of the protecting groups for the amino group include benzyloxycarbonyl, t-butoxycarbonyl, isobornyloxycarbonyl, and 9-fluorenylmethyloxycarbonyl.

Examples of the protecting groups for the guanidino group include nitro, benzyloxycarbonyl, tosyl, p-methoxybenzenesulfonyl, and mesitylensulfonyl.

Examples of the protecting groups for the mercapto group include trityl, acetamidomethyl, benzyl, p-methoxybenzyl, and 3-nitro-2-pyridinesulfenyl.

Examples of the activation of carboxyl group include symmetrical anhydride, mixed anhydride, azide and active ester (ester with alcohol e.g., pentachlorophenol, 2,4-dinitrophenol, cyanomethyl alcohol, p-nitrophenol, N-hydroxysuccinimide, N-hydroxy-5-norbornene-2,3-dicarboxyimide, N-hydroxyphthalimide, and 1-hydroxybenzotriazol). An example of the activation of amino group is phosphite-amide.

The reaction is generally carried out in a solvent such as chloroform, dichloromethane, ethyl acetate, N,N-dimethylformamide, dimethylsulfoxide, pyridine, dioxane, tetrahydrofuran, water, methanol and mixture of these solvents.

The reaction temperature may be in the range of approx. $-30°$ C. to $50°$ C.

The conditions for removing the protecting group of the peptide of the invention may differ depending on the type of blocking group, but the conditions should be able to release the blocking group without producing any effect on the peptide bonding.

The protecting group can be removed by acid treatment, for example, treatment with hydrogen chloride, hydrogen bromide, hydrogen fluoride, methanesulfonic acid, trifluoromethanesulfonic acid, trifluoroacetic acid, and mixture of these acids. Further, the reduction with sodium metal in liquid ammonia or catalytic hydrogenolysis over palladium-carbon can be employed. On the reaction for removing the protecting group by the above acid treatment, addition of cation scavenger such as anisole, phenol and thioanisole is advantageous.

After the reaction is complete, the prepared peptide of the present invention can be obtained by the conventional process for purification of peptides, for example, extraction, partition, reprecipitation, recrystallization or column chromatography.

Further, the peptides of the present invention can be converted into their functional derivatives or their pharmaceutically acceptable salts as described above in a conventional manner.

The peptides of the present invention show a strong nootropic effect in passive avoidance tests using rats as described hereinafter.

The peptides of the present invention are believed to be effective for the following diseases and can be used for prevention or treatment thereof: senile dementia (Alzheimer's dementia), cerebrovascular dementia, and dementia based on Alzheimer's disease, Pick's disease, Huntington's disease, Creutzfeldt-Jakob disease, Parkinson's disease, cerebellar myelic denatured disease.

The peptides of the present invention have an extremely low toxicity, and cause no death even by administration of extremely higher doses than their effective doses.

The peptides of the present invention may be used in their inner salt form, their functional derivatives, or salts thereof. No matter which form is used, the dose as and amount of the peptide of the formula (I) is preferably in the range of 1 ng/day to 1 mg/day per 1 kg of a patient. In the case of parenteral administration (excluding rectal administration), the dose preferably is in the range of 10 ng/kg to 100 $\mu$g/kg per day. In the case of oral administration and rectal administration, it is preferred that the dose should be 10 to 100 times more than that of the parenteral administration. The peptides of the present invention are mainly administered parenterally (e.g., intravenous or hypodermic injection, intracerebroventricular or intraspinal administration, nasal administration, and rectal administration). They can also be administered orally depending on the case.

The peptides of the present invention can be incorporated into pharmaceutical compositions in the form of injection liquid, suppository, powder, collunarium, granule and tablets. The peptides of the invention can be preserved as physiological saline solutions or can be freeze-dried in an ampule after addition of mannitol or sorbitol and are melted when they are used for administration.

Examples of the present invention are set forth hereinafter.

In each example, the eluants used for a thin-layer chromatography (TLC) were as follows. As for the solid phase, TLC Plate Silica Gel $60F_{254}$ by Merck Co., Ltd. was used.

$Rf^1$: chloroform-methanol-acetic acid-water (80:20:2.5:5) lower layer
$Rf^2$: chloroform-methanol-water (70:30:5)
$Rf^3$: n-butanol-acetic acid-water (2:1:1)

Further, purification by a high-performance liquid chromatography was carried out using the following materials:

Column: $\mu$Bondapak $C_{18}$ 1.9×15 cm
Mobile phase:
A) 0.05% trifluoroacetic acid (TFA)
B) acetonitrile

EXAMPLE 1 pGlu—Asn—Cys—Pro—D—Arg—Gly—NH₂ acetate
|
H—Cys—OH (1) Z-D-Arg(Mbs)-Gly—NH₂

In a mixture of 500 ml of ethyl acetate and 200 ml of 5% aqueous citric acid solution was dissolved 30 g of Z-D-Arg(Mbs)—OH dicyclohexylamine salt under stirring. The ethyl acetate portion was then washed with water, and dried over anhydrous sodium sulfate.

After the solvent was distilled off, the resulting residue was dissolved in 300 ml of N,N-dimethylformamide (DMF). To the solution were successively added under chilling with ice 5 g of H—Gly—NH$_2$ hydrochloride, 5 ml of N-methylmorpholin, 8 g of 1-hydroxybenzotriazole and 9.8 g of N,N'-dicyclohexylcarbodiimide. After the reaction mixture was stirred for 18 hours at room temperature, N,N'-dicyclohexylurea was removed from the mixture by filtration, and the filtrate was treated to distill off DMF.

The resulting residue was dissolved in 2-butanoldichloromethane (5:1 v/v), and the resulting solution was washed successively with a saturated aqueous sodium hydrogencarbonate solution, dilute hydrochloric acid saturated with sodium chloride and a saturated aqueous sodium chloride solution, and dried over anhydrous sodium sulfate.

The solvent was distilled off, and the residue was crystallized from methanol-ether to yield the desired compound by filtration.

Yield: 14.6 g.
M.P.: 194°–196° C.
Rf$^1$: 0.24, Rf$^2$: 0.52.
$[\alpha]_D$: $-2.9°$ (c=0.5, DMF).

(2) Boc-Pro-D-Arg(Mbs)-Gly—NH$_2$

To 200 ml of 80% acetic acid was added 10.7 g of Z-D-Arg(Mbs)-Gly—NH$_2$. The mixture was stirred for 6 hours in a stream of hydrogen in the presence of 10% palladium-carbon.

After palladium-carbon was removed by filtration, the solvent was distilled off from the filtrate. The residue was dried under reduced pressure and dissolved in 100 ml of DMF. To the resulting solution were added 3 ml of N-methylmorpholine and 6.2 g of Boc-Pro-OSu, and the mixture was stirred for 18 hours at room temperature.

After DMF was distilled off, the resulting residue was dissolved in 2-butanol-dichloromethane (5:1 v/v). The resulting solution was then washed successively with a saturated aqueous sodium hydrogencarbonate solution, dilute hydrochloric acid saturated with sodium chloride and a saturated aqueous sodium chloride solution, and dried over anhydrous sodium sulfate.

After the solvent was distilled off, the residue was crystallized from ether and collected by filtration to give the desired compound.

Yield: 11.9 g.
M.P.: 108°–111° C.
Rf$^1$: 0.32, Rf$^2$: 0.56.
$[\alpha]_D$: $-6.9°$ (c=0.5, DMF).

(3) Boc-Cys(Acm)-Pro-D-Arg(Mbs)-Gly—NH$_2$

To a mixture of 100 ml of tetrahydrofuran (THF) and 100 ml of 4N HCl-ethyl acetate was added 9 g of Boc-Pro-D-Arg(Mbs)-Gly—NH$_2$. The mixture was allowed to stand for 30 minutes at room temperature, and then treated to distill off the solvent.

The residue was dried under reduced pressure and was dissolved in 100 ml of DMF. To the resulting solution were successively added under chilling with ice 3.3 ml of N-methylmorpholin, 4.8 g of Boc-Cys(Acm)—OH, 2.4 g of 1-hydroxybenzotriazole and 3.4 g of N,N'-dicyclohexylcarbodiimide. The mixture was then stirred for 18 hours at room temperature.

N,N'-dicyclohexylurea was removed by filtration, and the filtrate was treated to distill DMF. The residue was dissolved in 2-butanol-dichloromethane (5:1 v/v), the resulting solution was successively washed with a saturated aqueous sodium hydrogencarbonate solution, dilute hydrochloric acid solution and a saturated aqueous saturated with sodium chloride, an aqueous sodium chloride solution, and dried over anhydrous sodium sulfate.

The solvent was distilled off, and the residue was crystallized by addition of ether and collected by filtration to yield the desired compound.

Yield: 9.8 g.
M.P.: 88°–90° C.
Rf$^1$: 0.21., Rf$^2$: 0.52.
$[\alpha]_D$: $-17.6°$ (c=0.5, DMF).

(4) Z-pGlu-Asn-Cys(Acm)-Pro-D-Arg(Mbs)-Gly—NH$_2$

To 20 ml of 2N HCl-acetic acid was added 6.3 g of Boc-Cys(Acm)-Pro-D-Arg(Mbs)-Gly—NH$_2$. After the mixture was allowed to stand for 30 minutes at room temperature, the solvent was distilled off.

The residue was dried under reduced pressure, and dissolved in 100 ml of DMF. To the resulting solution were successively added under chilling with ice 1 ml of N-methylmorpholin, 3.1 g of Z-pGlu-Asn—OH, 1.3 g of 1-hydroxybenzotriazole, and 1.8 g of N,N'-dicyclohexylcarbodiimide.

Having been stirred for 40 hours at room temperature, the reaction mixture was filtered to remove N,N'-dicyclohexylurea, and the filtrate was treated to distill off DMF.

In 2-butanol-dichloromethane (5:1 v/v) was dissolved the resulting residue, and the resulting solution was washed successively with a saturated aqueous sodium hydrogencarbonate solution, dilute hydrochloric acid saturated with sodium chloride and a saturated aqueous sodium chloride solution, and dried over anhydrous sodium sulfate.

The solvent was distilled off, and the residue was crystallized by addition of ether and collected by filtration to yield the desired compound.

Yield: 6.0 g.
M.P.: 161°–166° C.
Rf$^1$: 0.05 Rf$^2$: 0.31.
$[\alpha]_D$: $-35.0°$ (c=0.5, DMF).

(5) Z-pGlu-Asn-Cys(Scm)-Pro-D-Arg(Mbs)-Gly—NH$_2$

To a solution of 1.0 g of Z-pGlu-Asn-Cys(Acm)-Pro-D-Arg(Mbs)-Gly—NH$_2$ in 50 ml of dichloromethane-methanol (1:1 v/v) was added under chilling with ice 0.15 ml of carbomethoxysulfenyl chloride (Cl-Scm), and the mixture was stirred for 1 hour.

The solvent was distilled off. The residue was crystallized by addition of ether, and the crystals were collected by filtration to give the desired compound.

Yield: 1.0 g.
M.P.: 176°–180° C.
Rf$^1$: 0.11, Rf$^2$: 0.42.
$[\alpha]_D$: $-54.3°$ (c=0.5, DMF).

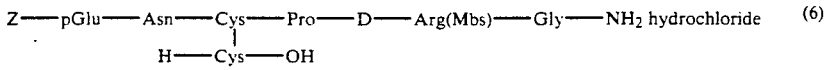
(6)

To a solution of 1.0 g of Z-pGlu-Asn-Cys(Scm)-Pro-D-Arg(Mbs)-Gly—NH₂ in 20 ml of DMF was added 0.38 g of cysteine hydrochloride. The mixture was stirred for 1 hour at room temperature.

The solvent was distilled off, and the residue was purified by a silica gel column chromatography using chloroform-methanol, and then crystallized by addition of ether. The precipitated crystals were collected by filtration to give the desired compound.
Yield: 0.68 g.
M.P.: 162°–166° C.
Rf²: 0.05.
$[\alpha]_D$: −37.9° (c=0.5, DMF).

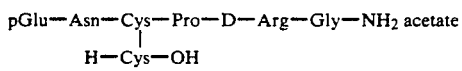
(7)

To a mixture of 4 ml of methanesulfonic acid and 0.4 ml of anisole was added 420 mg of

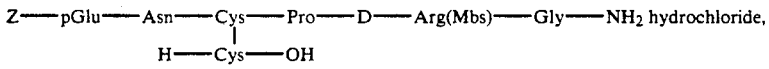

and the resulting mixture was stirred for 1.5 hours at room temperature. To the reaction mixture was added ether, and the supernatant portion of the mixture was removed. The precipitate was dissolved in water, the resulting solution was then subjected to Dowex 1×2 (acetate type) treatment, and the water was distilled off.

The residue was dissolved in 0.05% trifluoroacetic acid, and the solution was purified using a high performance liquid chromatography at 15 ml/min. (flow rate), and 0 to 10% B) 20 min. linear gradient (mobile phase). The resulting solution was treated with Dowex 1×2 (acetate type), and then freeze-dried to give the desired compound.
Yield: 80 mg.
Rf³: 0.07.
$[\alpha]_D$: −129.1° (c=0.6, water).

EXAMPLE 2 pGlu-Asn-Cys-Pro-Arg-Gly—NH₂ acetate (1) Z-Arg(Mbs)-Gly—NH₂
The procedure of (1) in Example 1 was repeated using 10 g of Z-Arg(Mbs)—OH dicyclohexylamine salt, 1.7 g of H-Gly—NH₂ hydrochloride, 1.7 ml of N-methylmorpholine, 2 g of 1-hydroxybenzotriazole and 3.4 g of N,N'-dicyclohexylcarbodiimide to give the desired compound.
Yield: 5.0 g.
M.P.: 201°–202° C.
Rf¹: 0.26, Rf²: 0.55.
$[\alpha]_D$: +2.1° (c=0.5, DMF).

(2) Boc-Pro-Arg(Mbs)-Gly—NH₂
The procedure of (2) in Example 1 was repeated using 20.8 g of Z-Arg(Mbs)-Gly—NH₂, 12.1 g of Boc-Pro-OSu and 4.3 ml of N-methylmorpholine to give the desired compound.
Yield: 21.5 g.
M.P.: 120°–126° C.

Rf¹: 0.31, Rf²: 0.53.
$[\alpha]_D$: −26.5° (c=1, DMF).

(3) Boc-Cys(MBzl)-Pro-Arg(Mbs)-Gly—NH₂
3.7 g of Boc-Pro-Arg(Mbs)-Gly—NH₂ was subjected to 4N HCl-ethyl acetate treatment in the same manner as (3) in Example 1 to remove Boc.

In 30 ml of DMF was dissolved the obtained H-Pro-Arg(Mbs)-Gly—NH₂ hydrochloride, and to the solution were successively added under chilling with ice 0.7 ml of N-methylmorpholin, 2.1 g of Boc-Cys(MBzl)—OH, 0.85 g of 1-hydroxybenzotriazole and 1.4 g of N,N'-dicyclohexylcarbodiimide. After stirring for 18 hours at room temperature, the reaction mixture was filtered to remove N,N'-dicyclohexylurea, and then the filtrate was treated to distill off DMF.

In CHCl₃ was dissolved the residue, the resulting solution was then washed successively with a saturated aqueous sodium hydrogencarbonate solution, dilute hydrochloric acid saturated with sodium chloride and a saturated aqueous sodium chloride solution, and dried over anhydrous sodium sulfate.

The solvent was distilled off, and ether was added to the resulting residue for crystallization. The crystals were collected by filtration to yield the desired compound.
Yield: 3.2 g.
M.P.: 104°–107° C.
Rf¹: 0.44, Rf²: 0.63.
$[\alpha]_D$: −27.9° (c=0.5, DMF).

(4) Z-pGlu-Asn-Cys(MBzl)-Pro-Arg(Mbs)-Gly—NH₂
To 10 ml of 2N HCl-acetic acid was added 1.8 g of Boc-Cys(MBzl)-Pro-Arg(Mbs)-Gly—NH₂. The mixture was allowed to stand for 30 min. at room temperature and then treated to distill off the solvent.

The residue was dried under reduced pressure, and then dissolved in 30 ml of DMF. To the resulting solution were added under chilling with ice 0.25 ml of N-methylmorpholine, 0.9 g of Z-pGlu-Asn—OH, 0.38 g of 1-hydroxybenzotriazole and 0.5 g of N,N'-dicyclohexylcarbodiimide.

After stirring for 40 hours, the mixture was filtered to remove N,N'-dicyclohexylurea, and then the filtrate was treated to distill off DMF.

In 2-butanol-dichloromethane (5:1 v/v) was dissolved the residue. The solution was washed successively with a saturated aqueous sodium hydrogencarbonate solution, dilute hydrochloric acid saturated with sodium chloride, and a saturated aqueous sodium chloride solution, and dried over anhydrous sodium sulfate.

The solvent was distilled off, and the residue was purified by silica gel chromatography using chloroform-methanol, and then crystallized by addition of ether and collected by filtration to give the desired compound.
Yield: 0.85 g.
M.P.: 131°–135° C.
Rf¹: 0.19; Rf²: 0.44.

[α]$_D$: −43.3° (c=0.6, DMF).

(5) pGlu-Asn-Cys-Pro-Arg-Gly—NH$_2$ acetate

To a mixture of 4 ml of methanesulfonic acid, 0.25 ml of anisol and 0.2 ml of ethanedithiol was added 440 mg of z-pGlu-Asn-Cys(MBzl)-Pro-Arg(Mbs)-Gly—NH$_2$, and the mixture was stirred for 1 hour at room temperature. To the mixture was added ether, and the supernatant portion of the mixture was removed. The precipitate was dissolved in water. The solution was subjected to Dowex 1×2 (acetate type) treatment, and then was treated to distill off the water.

The residue was dissolved in 0.05% trifluoroacetica

Rf$^1$: 0.09, Rf$^2$: 0.35.
[α]$_D$: −23.3° (c=0.5, DMF).

(4) Z-pGlu-Asn-Cys(Scm)-D-Pro-Arg(Mbs)-Gly—NH$_2$

The procedure of (5) in Example 1 was repeated using 1.0 g of Z-pGlu-Asn-Cys(Acm)-D-Pro-Arg(Mbs)-Gly—NH$_2$ and 0.15 ml of Cl-Scm to give the desired compound.
Yield: 0.9 g.
M.P.: 142°–147° C.
Rf$^1$: 0.20, Rf$^2$: 0.49.
[α]$_D$: −40.8° (c=0.5, DMF).

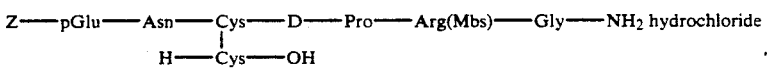

cid, the solution was purified using a high-performance liquid chromatography at 15 ml/min. (flow rate), 2 to 12% B) 20 min. linear gradient (mobile phase). The resulting solution was treated with Dowex 1×2 (acetate type) treatment and freeze-dried to give the desired compound.
Yield: 28 mg.
Rf$^3$ (including 1% ethanedithiol): 0.14.
[α]$_D$: −92.8° (c=0.5, water).

EXAMPLE 3

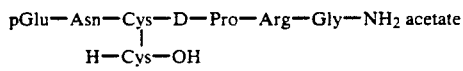

The procedure of (6) in Example 1 was repeated using 0.5 g of Z-pGlu-Asn-Cys(Scm)-D-Pro-Arg(Mbs)-Gly—NH$_2$ and 0.15 g of cysteine hydrochloride to give the desired compound.
Yield: 0.46 g.
M.P.: 162°–165° C.
Rf$^2$: 0.07.
[α]$_D$: −26.2° (c=0.5, DMF).

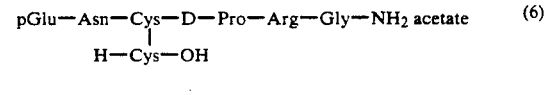

120 mg of

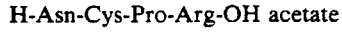

(1) Boc-D-Pro-Arg(Mbs)-Gly—NH$_2$

The procedure of (2) in Example 1 was repeated using 5.2 g of Z-Arg(Mbs)-Bly—NH$^2$, 3.1 g of Boc-D-Pro-OSu, and 2.2 ml of N-methylmorpholine to give the desired compound.
Yield: 5.7 g.
M.P.: 88°–91° C.
Rf$^1$: 0.35, Rf$^2$: 0.59.
[α]$_D$: +8.7° (c=0.6, DMF).

(2) Boc-Cys(Acm)-D-Pro-Arg(Mbs)-Gly—NH$_2$

The procedure of (3) in Example 1 was repeated using 2.5 g of Boc-D-Pro-Arg(Mbs)-Gly—NH$_2$, 1.3 g of Boc-Cys(Acm)—OH, 0.73 g of 1-hydroxybenzotriazole, 0.94 g of N,N′-dicyclohexylcarbodiimide and 1 ml of N-methylmorpholine to give the desired compound.
Yield: 2.2 g.
M.P.: 110°–114° C.
Rf$^1$: 0.22, Rf$^2$: 0.50.
[α]$_D$: −21.9° (c=0.5, DMF).

(3) Z-pGlu-Asn-Cys(Acm)-D-Pro-Arg(Mbs)-Gly—NH$_2$

The procedure of (4) in Example 1 was repeated using 2.0 g of Boc-Cys(Acm)-D-Pro-Arg(Mbs)-Gly—NH$_2$, 2.0 g of Z-pGlu-Asn—OH, 0.5 g of 1-hydroxybenzotriazole, 0.58 g of N,N′-dicyclohexylcarbodiimide and 0.5 ml of N-methylmorpholine to give the desired compound.
Yield: 1.8 g.
M.P.: 120°–124° C.

was subjected to methanesulfonic acid (MSA)-anisole treatment in the same manner as (7) in Example 1, and then purified by a high-performance liquid chromatograpy at 12 ml/min. (flow rate), 0 to 20% B) 20 min. linear gradient (mobile phase). The resulting solution was subjected to Dowex 1×2 (acetate type) treatment, freeze-dried to give the desired compound.
Yield: 53 mg.
Rf$^3$: 0.10.
[α]$_D$: −106.0° (c=0.5, water).

EXAMPLE 4

H-Asn-Cys-Pro-Arg-OH acetate (1) Boc-Pro-Arg(Mbs)-OBzl

To a solution of 14.2 g of H-Arg(Mbs)-OBzl hydrochloride in 200 ml of THF were added 3.3 ml of N-methylmorpholine and 9.4 g of Boc-Pro-OSu. The mixture was stirred for 18 hours at room temperature.

THF was distilled off, and the residue was dissolved in ethyl acetate. The solution was successively washed with an aqueous dilute hydrochloric acid, a saturated aqueous sodium hydrogencarbonate solution and water, and dried over anhydrous sodium sulfate.

The solvent was distilled off to give the desired compound as an oil.
Yield: 18 g.
Rf$^1$: 0.69, Rf$^2$: 0.86.
[α]$_D$: −29.6° (c=0.5, DMF).

(2) Boc-Cys(MBzl)-Pro-Arg(Mbs)-OBzl

To 15 ml of 4N HCl-ethyl acetate was added 3.7 g of Boc-Pro-Arg(Mbs)-OBzl. The mixture was allowed to stand for 30 minutes at room temperature, and the solvent was then removed by distillation. The residue was dried under reduced pressure, and then dissolved in 50 ml of DMF. To the solution were added under chilling with ice 1.4 ml of N-methylmorpholine, 2.2 g of Boc-Cys(MBzl)—OH, 0.95 g of 1-hydroxybenzotriazole and 1.3 g of N,N'-dicyclohexylcarbodiimide. After stirring 18 hours at room temperature, the reaction mixture was filtered to remove N,N'-dicyclohexylurea, and the filtrate was treated to distill off DMF.

The resulting residue was dissolved in 2-butanoldichloromethane (5:1 v/v), and the solution was washed successively with a saturated aqueous sodium hydrogen-carbonate solution, dilute hydrochloric acid saturated with sodium chloride and a saturated aqueous sodium chloride solution, and dried over anhydrous sodium sulfate.

The solvent was distilled off, and the residue was purified by silica gel chromatography using chloroform-methanol to yield the desired compound as an oil.
Yield: 4 g.
$Rf^1$: 0.82, $Rf^2$: 0.88.
$[\alpha]_D$: $-25.0°$ (c=0.5, DMF).

(3) Z-Asn-Cys(MBzl)-Pro-Arg(Mbs)-OBzl

To 5 ml of 4N HCl-ethyl acetate was added 1.7 g of Boc-Cys(MBzl)-Pro-Arg(Mbs)-OBzl. The mixture was allowed to stand for 30 min. at room temperature, and the solvent was removed. To the residue were added 2-butanoldichloromethane (5:1 v/v) and a saturated aqueous sodium hydrogencarbonate solution. The organic portion was taken out, and washed with a saturated aqueous sodium chloride solution, and dried over anhydrous sodium sulfate.

The solvent was distilled off, and the residue was dissolved in 30 ml of DMF. To the resulting solution were added under chilling with ice 0.58 g of Z-Asn-OH, 0.34 g of 1-hydroxybenzotriazole and 0.45 g of N,N'-dicyclohexylcarbodiimide. After stirring 18 hours at room temperature, N,N'-dicyclohexylurea was removed from the mixture by filtration and DMF was distilled of from the filtrate.

The residue was dissolved in 2-butanol-dichloromethane (5:1 v/v), and the solution was washed successively with a saturated aqueous sodium hydrogencarbonate solution, dilute hydrochloric acid saturated with sodium chloride and a saturated aqueous sodium chloride solution, and dried over anhydrous sodium sulfate.

After the solvent was distilled off, the residue was crystallized from ether, and the crystals were collected by filtration to yield the desired compound.
Yield: 1.8 g.
M.P.: 98°–100° C.
$Rf^1$: 0.70, $Rf^2$: 0.82.
$[\alpha]_D$: $-29.2°$ (c=0.5, DMF).

(4) H-Asn-Cys-Pro-Arg-OH acetate

To a mixture of 4 ml of methanesulfonic acid and 0.4 ml of anisol was added 100 mg of Z-Asn-Cys(MBzl)-Pro-Arg(Mbs)-OBzl. The mixture was stirred for 1.5 hour at room temperature and, after addition of ether, the supernatant portion of the solution was removed. The precipitate was dissolved in water. The solution was subjected to Dowex 1×2 (acetate type) treatment, and the water was distilled off.

The residue was dissolved in 0.05% trifluoroacetic acid, and the solution was purified by high-performance liquid chromatography at 12 ml/min. (flow rate), 0 to 10% B) 20 min. linear gradient (mobile phase) and subjected to Dowex 1×2 (acetate type) treatment to freeze-dry and to obtain the desired compound.
Yield: 47 mg.
$Rf^3$ (including 1% ethanedithiol): 0.18.
$[\alpha]_D$: $-54.6°$ (c=0.5, water).

Examples of pharmacological tests showing the effectiveness of the peptides of the present invention are set forth below.

Pharmacological Tests

The effect of peptides of the invention on memory consolidation was evaluated by conducting one-trial passive avoidance experiments using male Wistar rats in accordance with the method described by Burbach et al., Science, vol. 221, pp. 1310-1312, 1983. The apparatus was composed of an illuminated room and a dark room, and their floors were made of a stainless-steel grid. The rats placed in the illuminated room could freely enter the dark room. Upon entering the dark room the rats received an electro-shock. Retention of passive avoidance behavior to the electro-shock was determined by the measurement of a response latent period, i.e. the period required for the rat which experienced the electro-shock to re-enter the dark room from the time at which the rat was placed in the illuminated room after predetermined intervals.

(1) Examination on facilitation effect of memory consolidation

The rats were treated with the peptides of the invention obtained in the aforementioned Example 1 to 4 or a physiological saline solution by means of a subcutaneous injection immediately after receiving the electro-shock (0.25 mA). Then 24 hours later, the retention of the memory of the electro-shock was tested.

The rats administered with the physiological saline solution alone acted as a control group and generally showed a response latent period of approx. 50 seconds.

For comparison, the above same tests were conducted with the following known peptides.

Comparison Compound 1 (known peptide):

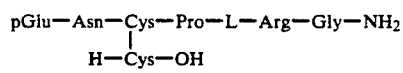

Comparison Compound 2 (known peptide):

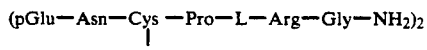

For each group, 6 to 8 rats were tested. The response latent period was measured up to a maximum of 600 seconds.

The dose and the effect (the ratio of the response latent period of each group to that of the control groups, shown as %) of the peptides obtained in each example and the peptides of each comparison compound are set forth in Table 1.

TABLE 1

| Group | Dose (ng/kg) | Effect (%) |
| --- | --- | --- |
| Example 1 | 1 | 267 |
| Example 2 | 1 | 295 |
| Example 3 | 1 | 253 |
| Example 4 | 1 | 316 |
| Comparison 1 | 10 | 313 |
| Comparison 2 | 10 | 249 |

2) Examination on improvement effect of experimental retrograde amnesia by cycloheximide The rats received an electro-shock (0.5 mA) one hr. after the administration of the peptides of the invention or a physiological saline solution. Immediately after receiving the electro-shock, the rats were treated with 2.7 to 3.0 mg/kg of cycloheximide or the saline solution by subcutaneous injection. At 48 hours after the administration was made, memory retention of the rats was tested. The rats administered with only the physiological saline solution showed a response latent period of approx. 300 seconds, and those rats of the control group administered with a physiological saline solution and treated with cycloheximide alone showed a response latent period of approx. 50 seconds, which revealed retrograde amnesia.

The average response latent period of rats administered with each peptide of the invention and treated with cycloheximide were compared with that of the control group. Six to eight rats were used for each group tested. The response latent period was measured up to a maximum of 600 seconds.

The dose and the effect (the ratio of response latent period of each group to that of the control groups, shown as %) of the peptides obtained in each example and the peptides of each comparison example are set forth in Table 2.

TABLE 2

| Group | Dose (ng/kg) | Effect (%) |
| --- | --- | --- |
| Example 1 | 1 | 302 |
| Example 2 | 1 | 633 |
| Example 3 | 1 | 380 |
| Example 4 | 1 | 320 |
| Comparison 1 | 10 | 583 |
| Comparison 2 | 100 | 503 |

As is readily apparent from the above experimental results, the peptides of the invention had the same effects as the known peptides at a dose of 1/10 to 1/100 of that of the known peptides and showed superior effect on the facilitation of memory consolidation as well as an effect on improving retrograde amnesia.

Although the structures of the peptides of the invention have similar structures to those of the known peptides, they are slightly different from those of the known peptides and these have a significant influence on memory consolidation effect of a peptide. The fact that these slight differences in the peptides of the invention produce a remarkable effect indicates that it is impossible to make an estimation on the memory consolidation effect of a peptide from its structure.

For example, although the peptide obtained in Example 1 possesses D-Arg in place of L-Arg of the peptide of Comparison Compound 1 and the rest of the structure of each peptide is identical, the peptide obtained in Example 1 showed the same effect to that of Comparison Compound 1 with only 1/10 of the dose, which testifies to the fact the peptide obtained in Example 1 has superior effectiveness to the known peptide.

PREPARATION EXAMPLE 1 (INJECTION)

To 100 ml of a distilled water were added 0.1 mg of the peptide obtained in Example 1 and 0.9 g of sodium chloride to prepare an aqueous solution whose pH was adjusted to 6.0 to 8.0 with sodium hydroxide for injection. The solution was filtered under sterile condition, and the filtrate was filled up into 1 ml ampul. The ampul was fused to seal under sterile condition by heating to prepare an agent for injection.

PREPARATION EXAMPLE 2 (FREEZE-DRIED AGENT)

To 100 ml of a distilled water were added 5 mg of the peptide obtained in Example 1 and 5 g of D-mannitol to prepare an aqueous solution of which pH was adjusted to 6.0 to 8.0 with a phosphate buffer for injection. The solution was filtered under sterile conditions and the filtrate was divided into a plurality of 1 ml vials. The divided portions were freeze-dried to prepare a freeze-dried agent for injection.

PREPARATION EXAMPLE 3 (COLLUNARIUM)

To 100 ml of a physiological saline solution was added 10 mg of the peptide obtained in Example 1. The pH of the mixture was adjusted to 3.0 to 6.0 with a citric acid buffer to prepare a collinarium which contains 50 μg of the peptide of the invention in a dose of 0.5 ml.

PREPARATION EXAMPLE 4 (SUPPOSITORY)

To 98.5 g of hard fat (triglyceride of saturated fatty acid) was added 0.5 of egg york lecithin. The mixture was melted at temperature of 40° to 45° C. and to the melted mixture was added under stirring a solution of 5 mg of the peptide (obtained in Example 1) in 1 g of Polyethylene glycol (PEG) 400. The resulting dispersion (1 g) was filled into the mold for producing a suppository. The content was removed from the mold after being caked to prepare a suppository.

We claim:

1. A peptide having the formula (I):

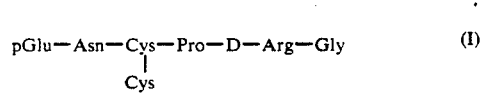

or its derivative having an amide group at the terminal amino acid moiety, or a pharmaceutically acceptable salt thereof.

2. A peptide having the formula (II):

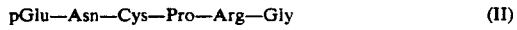

or its derivative having an amide group at the terminal amino acid moiety, or a pharmaceutically acceptable salt thereof.

3. A peptide having the formula (III):

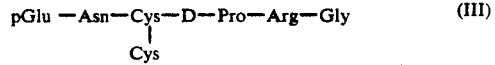

or its derivative having an amide group at the terminal amino acid moiety, or a pharmaceutically acceptable salt thereof.

4. A peptide having the formula (IV):

or its derivative having an amide group at the terminal amino acid moiety, or a pharmaceutically acceptable salt thereof.

5. A composition comprising an anti-dementia effective amount of the peptide, derivative or salt of claim 1 and a pharmaceutically acceptable carrier therefore.

6. A composition comprising an anti-dementia effective amount of the peptide, derivative or salt of claim 2 and a pharmaceutically acceptable carrier therefore.

7. A composition comprising an anti-dementia effective amount of the peptide, derivative or salt of claim 3 and a pharmaceutically acceptable carrier therefore.

8. A composition comprising an anti-dementia effective amount of the peptide, derivative or salt of claim 4 and a pharmaceutically acceptable carrier therefore.

9. The composition of claim 5 in the form of an injectable liquid, a collunarium or a suppository.

10. The composition of claim 6 in the form of an injectable liquid, a collunarium or a suppository.

11. The composition of claim 7 in the form of an injectable liquid, a collunarium or a suppository.

12. The composition of claim 8 in the form of an injectable liquid, a collunarium or a suppository.

13. A method for the treatment of dementia comprising administering to a patient, an anti-dementia effective amount of the composition of claim 5.

14. A method for the treatment of dementia comprising administering to a patient, an anti-dementia effective amount of the composition of claim 6.

15. A method for the treatment of dementia comprising administering to a patient, an anti-dementia effective amount of the composition of claim 7.

16. A method for the treatment of dementia comprising administering to a patient, an anti-dementia effective amount of the composition of claim 8.

* * * * *